United States Patent [19]

Herbert et al.

[11] Patent Number: 4,551,130
[45] Date of Patent: Nov. 5, 1985

[54] SURGICAL DRAINAGE AND IRRIGATION APPARATUS FOR POST OPERATIVE PATIENT CARE

[76] Inventors: William B. Herbert, RD #2, Box 448, Pine Bush, N.Y. 12566; Rohit A. Patel, 39 Gregory Dr., Goshen, N.Y. 10924

[21] Appl. No.: 608,244

[22] Filed: May 8, 1984

[51] Int. Cl.$^4$ ............................................. A61M 1/00
[52] U.S. Cl. ........................................ 604/32; 604/27; 604/247; 604/248; 604/256
[58] Field of Search .................. 604/32, 27, 248, 247, 604/256; 137/625.48

[56] References Cited

U.S. PATENT DOCUMENTS

| | | | |
|---|---|---|---|
| 1,633,074 | 6/1927 | Mott | 604/32 |
| 2,148,541 | 2/1939 | Dierker | 128/227 |
| 2,538,215 | 1/1951 | Stack | 128/227 |
| 3,233,609 | 2/1966 | Leucci | 128/227 |
| 3,780,736 | 12/1973 | Chen | 128/231 |
| 4,020,840 | 5/1977 | Barsom | 128/276 |
| 4,069,814 | 1/1978 | Clemens | 128/2 F |
| 4,397,335 | 8/1983 | Doblar et al. | 604/32 |

Primary Examiner—D. E. Gantz
Assistant Examiner—Chung K. Pak
Attorney, Agent, or Firm—Albert F. Kronman

[57] ABSTRACT

A post-operative patient drainage and irrigation apparatus, employing a simplified two-position valve to control the passage of fluids into and out of the body of the patient. A two-channel catheter directs body fluids into and out of the control valve. A first flexible tube directs irrigating solutions from a source into the control valve. A second flexible tube, attached at one end to the control valve, serves as a waste conduit from the said valve to a waste receptacle. Check valves carried in rubber squeeze bulbs in the first and second flexible tubes further control the direction of fluid flow and serve to clear obstructions in the apparatus. A simple control changes the two-position control valve position from one mode to another.

8 Claims, 5 Drawing Figures

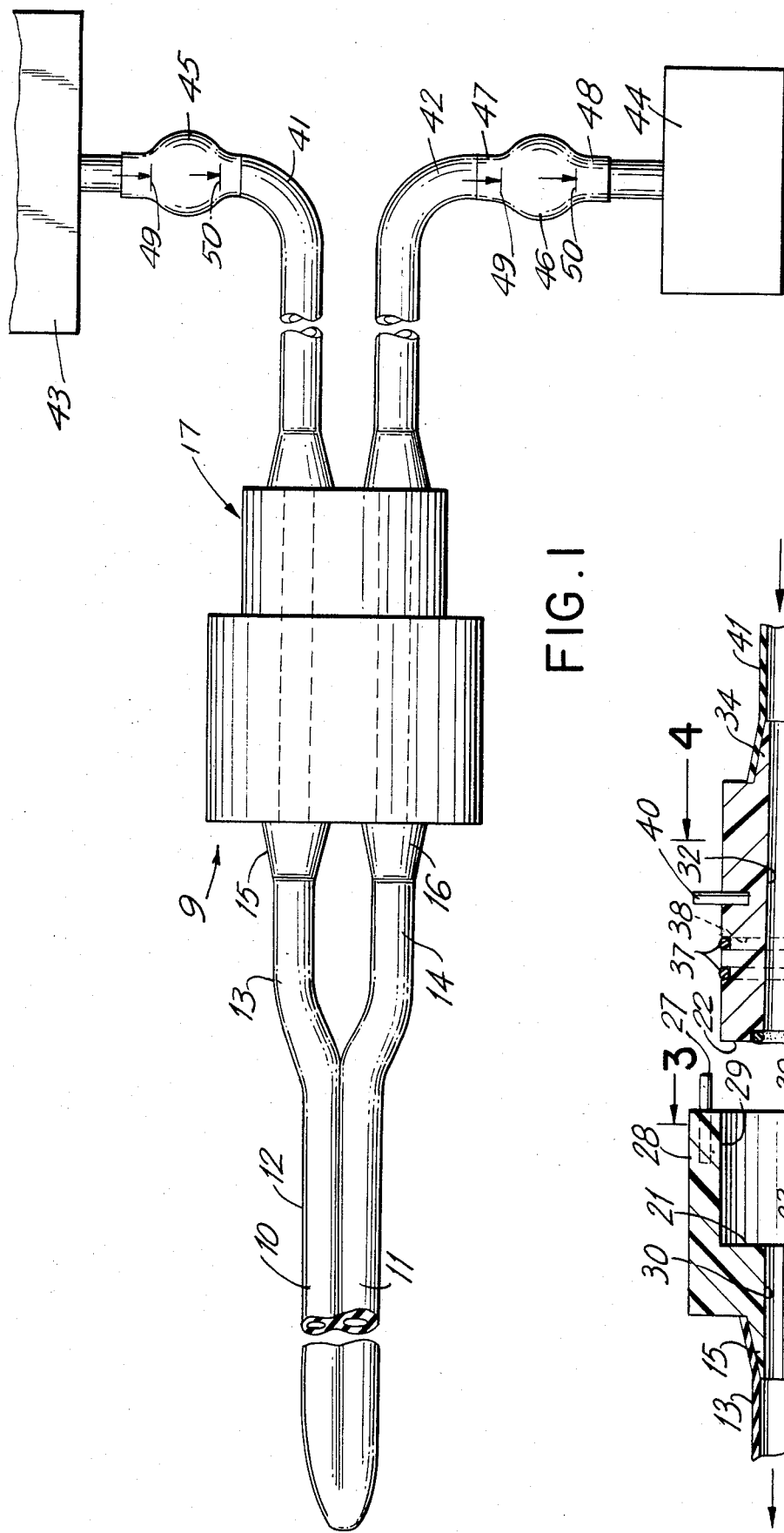
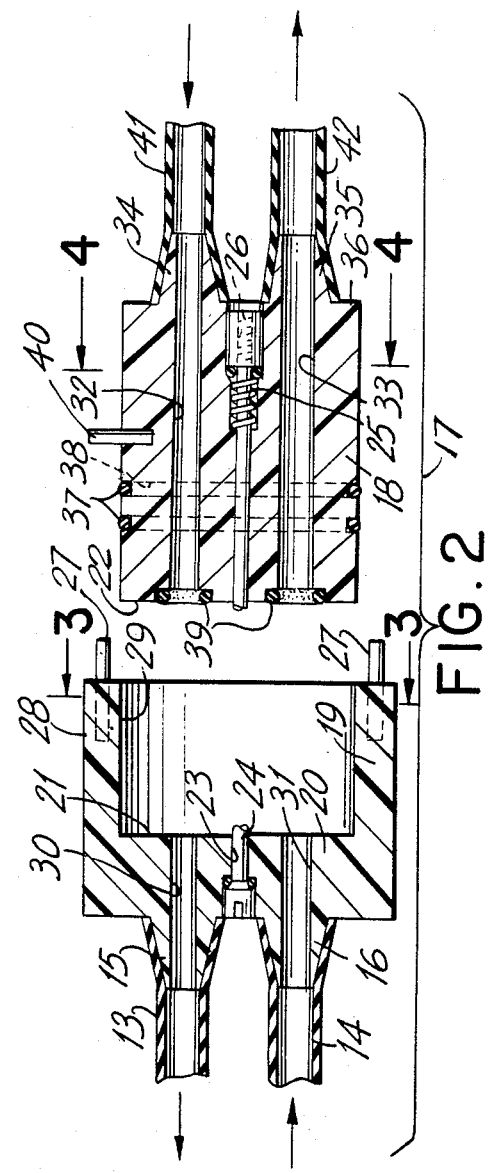
FIG. 1
FIG. 2

SURGICAL DRAINAGE AND IRRIGATION APPARATUS FOR POST OPERATIVE PATIENT CARE

BACKGROUND OF THE INVENTION

Present post-operative treatment following prostatic surgery or other surgical procedures involves the use of a gravity feed of saline or other solution through a multiple channel catheter feeding through the urinary tract into the bladder and draining waste through a second channel of the catheter. Blood clots or other matter tend to clog the waste channel or control value, causing a pressure build up in the bladder with resulting patient discomfort. Present practice and apparatus require a nurse or well-trained technician to disconnect the tubing from the gravity feed supply and the waste channel. A syringe filled with solution from a separate supply of solution is then connected to the waste channel and pressure is applied alternately with suction to dislodge the blockage. This pressure applied to an already pressurized bladder results in further patient discomfort, in addition to that caused by the disconnecting and reconnecting of tubing to the catheter which dilates the urinary tract to a degree that is painful. Previous practice also involved taping the catheter to the patients thigh. This practice was discontinued.

There are numerous patents relating to this art and many of these are directed to valve structures designed for systems of this type. This background disclosure is restricted to those patents which are believed most relevant.

One patent of interest is U.S. Pat. No. 2,148,541 which shows the use of suction means connected to valves in a colon therapy device for alternately expanding and contracting a part of the colon while fluid is circulating.

U.S. Pat. No. 3,780,736 discloses a surgical valve assembly for urinary bladder irrigation in which the valve core of a four-way valve is rotated to establish communication between the second and fourth ports of the valve to enable a quantity of irrigating fluid to be drawn into a receptacle; then to interconnect the first and fourth ports to successively discharge the irrigating fluid into the urinary tract and withdraw the same from the urinary tract back into the receptacle; then to interconnect the third and fourth ports to discharge from the receptacle the irrigated fluid and the matter withdrawn therewith from the urinary tract and into the urinary bag; finally to interconnect the first and third ports of the valve to permit conventional drainage from the urinary tract into urinary drainage bag.

U.S. Pat. No. 4,020,840 discloses a device for cathetherising the bladder, comprising catheter conduit means and pump means through which the flow direction of transported fluid is reversible in both means, a first pump connection connecting the pump means to the catheter means, valve means, a second pump connection connecting the pump means to the valve means, a return conduit means for communicating with a liquid container containing a liquid to be returned to the bladder, the valve means being operable to selectively arrange communication between the second pump connection and one of the discharge means and return conduit means in dependence on the delivery direction of the pump.

U.S. Pat. No. 3,233,609 is very basic, as it concerns irrigation apparatus for connecting a sterile fluid source and a waste container to a catheter comprising catheter means; a first substantially straight tubular member connected to a sterile fluid source, a second substantially straight tubular member positioned adjacent to and in parallel allignment with the first tubular member, the adjacent openings of the first and second tubular members being fused to form a common passageway coupled to the catheter means, the remaining opening of the second tubular member being adapted to pass sterile fluid to a waste container, said first and second tubular members being formed of a flexible material to permit manual manipulation of said tubular members for removal of obstructions occurring in the apparatus during the irrigation operation, the inner diameters of the tubular members each being greater than the inner diameter of the catheter, first and second clamping means connected to the remaining openings of the first and second tubular member respectively, for controlling the flow of this fluid source, the clamping means being adapted to cooperate with the first and second tubular members to facilitate the removal of constrictions occurring in the apparatus; adhesive means for joining the first and second tubular members along substantially all of their entire lengths to facilitate manipulation thereof.

As will be seen hereinafter, none of the above patents disclose, hint or suggest in any manner the herein described highly simplified, easily operated system.

Accordingly, it is an object of this invention to provide a simiplified irrigation and drainage system which can be used by relatively unskilled hospital personnel or by the patient as required, without danger or excessive discomfort to the patient.

An equally important object of this invention is to provide a closed system of this type which eliminates the need for repeated disconnecting and reconnecting of tubes, catheters, syringes and separate supplies of solution and thus reduces the possibility of infection.

A further object of the present invention is to provide an inexpensive, yet reliable, disposable control valve for the apparatus in combination with fluid conducting tubes having compressible bulbs and check valves useful in clearing obstructions.

SUMMARY OF THE INVENTION

This invention relates to a disposable assembly for selectively catheterizing, irrigating and draining the bladder or other body cavity. It may be used by persons with little or no medical supervision.

More specifically, the invention concerns an assembly of the character described which incorporates a two-position, highly-simplified valve having a cylindrical body core and a distributor rotatably carried on said core. Flexible tubes for interconnecting a two-lumen catheter with a source of solution and a fluid drainage bag are connected to the control valve. Compressible rubber bulbs including check valves are incorporated in the flexible tubes.

BRIEF DESCRIPTION OF THE DRAWINGS

FIG. 1 is a somewhat diagrammatic view, showing the essential elements of the present invention;

FIG. 2 is a partially exploded longitudinal sectional view of a valve assembly useful in the present invention;

DETAILED DESCRIPTION

Figure 3:
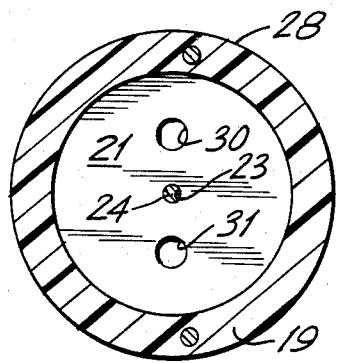
FIG. 3 is a cross-sectional view of the valve taken on line 3—3 of FIG. 2.
Figure 4:
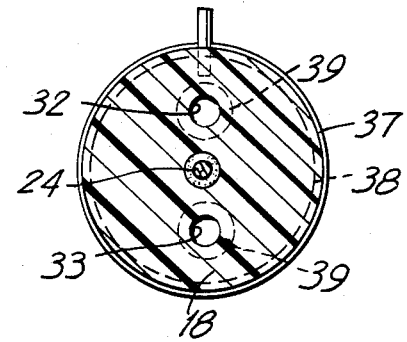
FIG. 4 is a cross-sectional view taken on line 4—4 of FIG. 2.

Referring to the drawings, FIG. 1 shows the entire surgical drainage and irrigation system 9 of the present invention. A catheter 10 is formed with two lumens 11,12. The catheter 10 is split into two short tubular portions 13,14 at its distal end for connection to a control valve generally indicated at 17 in FIG. 2. The control valve is provided with two ports 15,16 to receive the tubular portions 13,14. The valve 17 is formed of a suitable rigid material such as caprolactam, polymethacrylic, polystyrene or other suitable, inexpensive, organoplastic material.

As best shown in FIGS. 2–5, the valve 17 contains only two parts; a valve core 18 of cylindrical shape and a distributor 19 rotatably carried on the said core. The distributor 19 has an end wall 20 with an inner face 21 which is in wiping contact with the inner end 22 of the valve core 18 when the valve 17 is assembled. The end wall 20 is centrally bored as indicated at 23 to receive therethrough an elongated axial bolt 24. The bolt extends through the valve core 18 by way of a second axial bore 25 in said core. A small nut 26 is threaded upon the end of the bolt and serves to secure the control valve in its assembled condition while permitting the core and distributor to be rotated with respect to each other as hereinafter more fully described. Two small pins 27 are carried by the skirt portion 28 of the distributor 19 and extend outwardly therefrom so as to overlie the valve core 18 of the control valve 17. Spaced bores 30, 31 complete the structure of the distributor. The bores 30, 31 extend through end wall 20 and ports 15,16.

The valve core 18 is cylindrical in shape and preferably made of a solid block of plastic and of a diameter which will rotatably fit within the cylindrical cavity 29 formed by the end wall 20 and the skirt portion 28 of the distributor. Spaced longitudinal bores 32,33 extend through the valve core 18 and are separated from each other a distance which will bring them into register with the bores 30,31 when the control valve 17 is assembled as hereinafter more fully set forth. The longitudinal bores 32,33 also traverse two ports 34,35 on the outer end 36 of the valve core 18.

In order to insure the fluid tight integrity of the control valve 17, spaced "O" rings 37 are carried in recesses 38 in the outer surface of the valve core 18. In addition, the inner end 22 of the valve core 18 around the bores 32,33 is recessed to receive rubber elastomeric "O" rings 39 which extend slightly beyond said end so as to make good fluid tight contact with the surface of end wall 20 when the valve is assembled.

A small limit pin 40 carried by the valve core 18 extends outwardly therefrom so as to lie in the path of pins 27 carried by the distributor 19. By reason of the location of the pins 27,40 the rotation of the core with respect to the distributor is limited to a travel of 180 degrees, at each end of which the bores 30,31 will be in communication with the bores 32,33 as hereinafter more fully explained.

Figure 5:
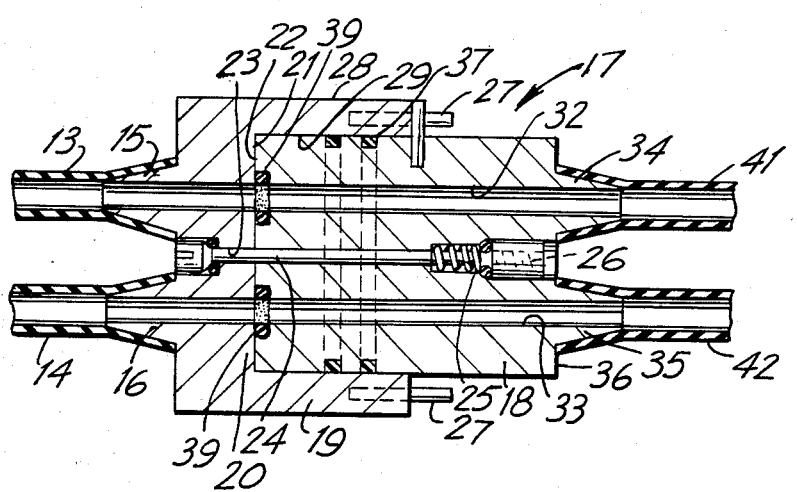
FIG. 5 is a view similar to FIG. 2 showing the valve in the assembled condition.

Flexible tubes 41,42 made of surgical rubber or a suitable plastic material well-known in the catheter art are secured to the ports 34,35 as shown in FIGS. 2 and 5. Tube 41 may be connected to a source of fluid 43 such as a saline solution for body cavity irrigating purposes, as indicated in FIGS. 1, and tube 42 may be in communication with a waste receptacle 44.

Referring to FIG. 1 it will be seen that a squeeze bulb 45,46 is incorporated into each of the tubes 41,42. The squeeze bulbs are well-known in the surgical art and are made of rubber or plastic and provided with inlet and outlet ports 47,48. The squeeze bulbs of the present invention, however, have check valves 49,50 incorporated therein so that when the bulb 45 or 46 is squeezed and released a suitable sucking force is applied to the inlet side of the tubing and a pressure is directed at the outlet side of the tubing. This action serves to clear any material which may be clogging the apparatus. During normal use fluid may pass freely through the tubes and squeeze bulbs 45,46. The check valves 49–50 allow clots, etc. to pass freely.

With the apparatus assembled as shown in FIGS. 1 and 5 and the catheter 10 in place, the irrigating solution will flow from the supply source, through tube 41, squeeze bulb 45 through bores 32,30 and into the body cavity (not shown) from the lumen 12. Waste fluid from the body cavity will flow through the lumen 11 of the catheter into the control valve bores 31,33 and to the waste receptacle 44 via the tube 42 and its squeeze bulb 46.

In the event the patient experiences internal pressure or any indication of blockage in the apparatus, the nurse, technician or even the patient will rotate the valve core 18, 180 degrees with respect to the distribution 19 by twisting them upon the bolt 24 until they come to a stop by reason of the location of pins 27,40. The bore 32 in the valve core will then be in communication with the bore 31 in the distributor 19. The irrigation fluid will then reverse flush the body cavity and waste fluid will exit via distributor bore 30 which is in communication with valve core bore 33. Squeeze bulb 46 may also be operated to apply a slight suction to additionally relieve the pressure and clear the lumens and tubes of any stoppage. Squeeze bulb 45 will force irrigation fluid through lumen 11 to clear lumen 11 of blockage and break up such blockage. Thereafter, the control valve 17 may be rotated again to bring it back to its original position.

If it is necessary to stop the flow of irrigation fluid, the rotation of the valve elements can be stopped at the 90 degree point so that the bores 30,32,31,34 are not in communication.

It will be apparent that the highly simplified structure of the above described apparatus lends itself to inexpensive construction and great reliability. Its cost can be low enough to make it a disposable item. Its light weight will enable the patient to secure it to a belt so that the patient can be ambulatory. Since the position of the control valve is limited by the stops to two positions, it can be operated by persons with a minimum training.

Having thus fully described the invention, what is desired to be claimed and secured by Letters Patent is:

1. A post-operative drainage and irrigation apparatus comprising a control valve, a substantially cylindrical core member in said valve having a longitudinal axis, a distributor rotatably secured to the core member and overlying at least a portion of said core, a first and a second spaced bore longitudinally traversing the valve core parallel to but spaced from the said longitudinal axis, a third and a fourth spaced bore in the distributor parallel to but spaced from the longitudinal axis, said first and second bores and third and forth bores being spaced from each other a distance which will bring them into alignment within the control valve in at least two rotation modes of the valve core with respect to the distributor, a first and a second port on the valve core in communication with the first and second bores in said core, a third and fourth port on the distributor in communication with the third and fourth bore in the distributor, stop means carried by the valve core and the distributor to limit the rotation of said core and distributor with respect to each other, a catheter for attachment to the control valve, a first and a second lumen formed within the catheter, said catheter having a proximal end for insertion within a body cavity and a distal end for attachment to the ports of the control valve distributor, a source of irrigation solution, a first flexible tube interconnecting the solution source with one of the ports on the valve core, normally open squeeze bulb valve means incorporated into the said tube between the solution source and control valve, a second flexible tube connected at one end to the other port of the valve core and adopted to discharge liquid coming out of said port, a second normally open squeeze bulb valve means incorporated into said second tube and means carried within the control valve to prevent liquid passing through the valve bores from escaping from between the valve core and distributor at all modes of valve operation.

2. Apparatus according to claim 1 in which the distributor is formed with a cylindrical cavity and an end wall in said cavity to receive at least a portion of the valve core therein.

3. Apparatus according to claim 1 in which the control valve is axially bored to receive an elongated bolt therethrough to secure the valve core and distributor in operative relationship.

4. Apparatus according to claim 1 in which the valve core is formed with annular grooves in its outer diameter disposed within the distributor to receive elastomeric rings in sealing contact with the said distributor.

5. Apparatus according to claim 1 in which the stop means comprise at least two spaced outwardly extending pins carried by the valve core and at least two spaced pins carried by the distributor disposed in the path of said outwardly extending pins.

6. Apparatus according to claim 2 in which the axial bore in the distributor is open at one end to receive the valve core and closed at its other end by an end wall.

7. Apparatus according to claim 6 in which the end of the valve core facing the end wall is substantially flat and in substantially wiping contact with the said end wall.

8. Apparatus according to claim 7 in which the flat portion of the valve core facing the distributor is recessed around the first and second bores to receive elastomeric "O" rings.

* * * * *